(12) United States Patent
Fujimoto et al.

(10) Patent No.: US 9,176,049 B2
(45) Date of Patent: Nov. 3, 2015

(54) METHOD OF OPTICAL ANALYSIS USING REFERENCE CELL AND BASE PLATE CORRECTION AND APPARATUS THEREOF

(75) Inventors: Koji Fujimoto, Kyoto (JP); Kotaro Shinozaki, Kyoto (JP); Shigeru Kitamura, Kyoto (JP)

(73) Assignee: Arkray Inc (JP)

( * ) Notice: Subject to any disclaimer, the term of this patent is extended or adjusted under 35 U.S.C. 154(b) by 1230 days.

(21) Appl. No.: 12/734,067

(22) PCT Filed: Oct. 29, 2008

(86) PCT No.: PCT/JP2008/069686
§ 371 (c)(1),
(2), (4) Date: Apr. 8, 2010

(87) PCT Pub. No.: WO2009/057659
PCT Pub. Date: May 7, 2009

(65) Prior Publication Data
US 2010/0209964 A1 Aug. 19, 2010

(30) Foreign Application Priority Data

Oct. 30, 2007 (JP) ................................. 2007-282001

(51) Int. Cl.
*G01N 21/00* (2006.01)
*G01N 21/25* (2006.01)
(Continued)

(52) U.S. Cl.
CPC .............. *G01N 21/253* (2013.01); *G01N 21/07* (2013.01); *G01N 21/78* (2013.01); *G01N 2021/0325* (2013.01)

(58) Field of Classification Search
CPC .............. G01N 2021/6463; G01N 2021/6482; G01N 21/0303; G01N 2201/064; G01N 33/5008; G01N 21/6452; G01N 35/028; B01L 3/5025; B01L 3/5027; B01L 2300/0829; B01L 2300/0893; B01L 2300/0825; B01L 2300/087
See application file for complete search history.

(56) References Cited

U.S. PATENT DOCUMENTS 3,526,480 A    9/1970  Findl et al.
3,953,136 A *  4/1976  Hach .............................. 356/410
(Continued)

FOREIGN PATENT DOCUMENTS

JP    06-066808 A    3/1994
JP    2007-187445    7/2007
(Continued)

OTHER PUBLICATIONS

International Search Report mailed on Dec. 2, 2008.

*Primary Examiner* — Yelena G Gakh
(74) *Attorney, Agent, or Firm* — Fishman Stewart Yamaguchi PLLC

(57) ABSTRACT

A method for analyzing a sample includes the step of irradiating a reaction portion of a sample BL and a reagent 40 in a reaction cell 34A of an analysis unit with light to obtain data D0 indicating optical characteristics of this portion. The method further includes the steps of irradiating a reference cell 34B which is not provided with a reagent 40 with light in a state in which the sample BL is supplied to the cell to obtain reference data D1 indicating optical characteristics of this portion, irradiating a base portion 34C of the analysis unit with light to obtain reference data D2 indicating optical characteristics of this portion, and obtaining data D3 indicating optical characteristics of the sample BL before reaction with the reagent 40 based on the reference data D1 and D2.

12 Claims, 7 Drawing Sheets

(51) Int. Cl.
   *G01N 21/07*  (2006.01)
   *G01N 21/78*  (2006.01)
   *G01N 21/03*  (2006.01)

(56) References Cited

U.S. PATENT DOCUMENTS

| | | | |
|---|---|---|---|
| 6,399,952 B1 * | 6/2002 | Maher et al. | 250/458.1 |
| 6,586,257 B1 * | 7/2003 | Vuong | 436/165 |
| 6,638,483 B2 * | 10/2003 | Vuong | 422/82.05 |
| 6,814,933 B2 * | 11/2004 | Vuong | 422/82.05 |
| 7,854,891 B2 * | 12/2010 | Yamamoto et al. | 422/63 |
| 2005/0112025 A1 * | 5/2005 | Takahashi et al. | 422/64 |
| 2008/0070318 A1 | 3/2008 | Yamamoto et al. | |

FOREIGN PATENT DOCUMENTS

| | | |
|---|---|---|
| WO | WO-2006/104005 A1 | 10/2006 |
| WO | WO-2007/001084 A1 | 1/2007 |

* cited by examiner

FIG. 4
FIG. 4A
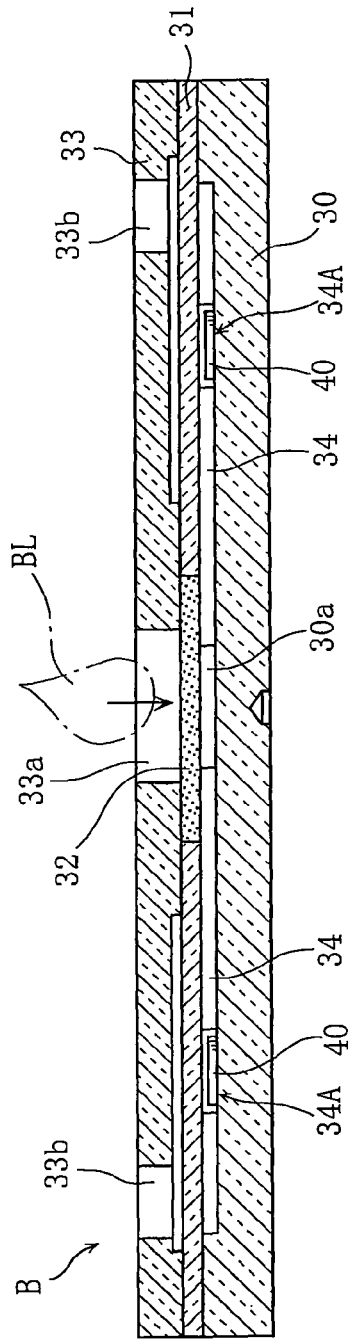
FIG. 4B
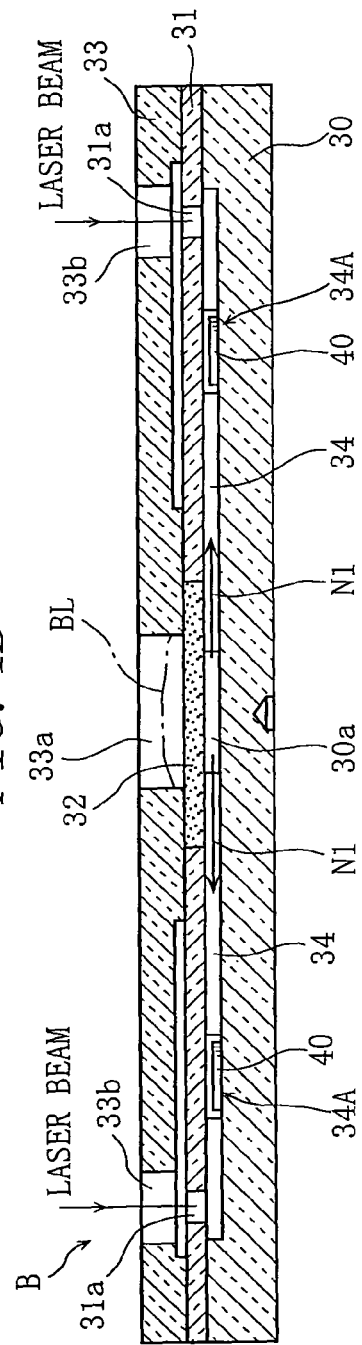

METHOD OF OPTICAL ANALYSIS USING REFERENCE CELL AND BASE PLATE CORRECTION AND APPARATUS THEREOF

TECHNICAL FIELD

The present invention relates to an analyzer and a method for analyzing a sample such as blood by using an optical technique.

BACKGROUND ART

In a conventional method to analyze a sample by using an optical technique, use is made of an analysis unit including a cell in which a reagent is provided (see e.g. Patent Document 1). In this method, a sample is supplied into the cell and reacted with the reagent. The reaction portion of the sample and the reagent is irradiated with light, whereby optical data on the reaction portion such as the amount of light transmitted or reflected are obtained. The sample is analyzed based on these data.

In this method, the sample is often diluted before it is reacted with the reagent. Since the color of the sample becomes lighter due to the dilution, the optical data on the above-described reaction portion are not largely influenced by the color of the sample. Correction processing called "blank correction" is also often performed in this method. Specifically, in the blank correction, a cell provided with a reagent but not provided with a sample is irradiated with light, whereby optical data (blank correction data) on this portion are obtained. By utilizing these data, the optical data on the reaction portion are corrected.

However, the above-described conventional analysis method has the following drawbacks.

In the conventional method, the sample itself is not precisely analyzed before the reaction with the reagent. Thus, even if the sample is not normal (for example, if the color or concentration of the sample is abnormal), the analysis of the sample is still performed, with such abnormalities overlooked. Specifically, in the case where the sample is blood, the blood is yellow when it has a high bilirubin content, red when it is hemolysis and milky white when it is chyle. In the conventional analysis method, even when the sample blood has such an abnormal color, the abnormality is not detected in advance, and the sample blood is analyzed by the reaction with a reagent anyway. Thus, there is a possibility that although the blood itself is abnormal, the abnormality is overlooked and the analysis is regarded as correct. When the blood is diluted before the reaction with the reagent, the above-described color abnormalities are more likely to be overlooked.

The reagent can be provided in a cell of the analysis unit in various manners. For instance, the reagent may be provided in the form of a solid in the cell, so that the surface of the reagent may readily scatter and reflect light. The reagent may include a high content of a substance which has a high absorbance. In these cases, when the cell is irradiated with light to obtain the above-described blank correction data, the light is scattered and reflected by the reagent or easily absorbed by the reagent. As a result, the amount of light which passes through the cell reduces. The blank correction data obtained based on such a small amount of light transmission tends to be incorrect, so that it is difficult to properly correct the optical data on the above-described reaction portion.

Patent Document 1: U.S. Pat. No. 3,526,480

DISCLOSURE OF THE INVENTION

Problems to be Solved by the Invention

An object of the present invention is to provide a sample analysis method and an analyzer capable of eliminating or lessening the above-described drawbacks.

Means for Solving the Problems

According to a first aspect of the present invention, there is provided a method for analyzing a sample by using an analysis unit including at least one reaction cell provided with a reagent. The method includes the step of irradiating a reaction portion of a sample and the reagent with light to obtain data indicating optical characteristics of the reaction portion when the reaction portion is formed due to supply of the sample to the reaction cell. The method further includes the steps of: irradiating a reference cell, which is formed in the analysis unit and which is not provided with a reagent, with light, wherein the reference cell is in a state in which the sample is supplied to the reference cell to obtain first reference data indicating optical characteristics of the reference cell; irradiating a base portion defined in the analysis unit with light to obtain second reference data indicating optical characteristics of the base portion, the base portion being a portion of the analysis unit at which the reaction cell and the reference cell are not formed and which has a substantially same sectional structure as a portion formed with the reference cell except for the absence of a cell; and obtaining data on the unreacted sample indicating optical characteristics of the sample before reaction with the reagent based on the first and the second reference data.

Preferably, the method for analyzing a sample according to the present invention further includes the step of determining whether or not the color or concentration of the sample is normal based on the data on the unreacted sample.

Preferably, the method for analyzing a sample according to the present invention further includes the step of correcting the optical data on the reaction portion by utilizing the first reference data to obtain more precise optical data on the reaction portion.

According to a second aspect of the present invention, there is provided an analyzer including an optical measurement means which is capable of, with an analysis unit including at least one reaction cell provided with a reagent set at a predetermined position, irradiating a reaction portion of a sample and the reagent with light to obtain data indicating optical characteristics of the reaction portion when the reaction portion is formed by supplying the sample to the reaction cell, and a data processor for processing the data. When the analysis unit includes a reference cell which is not provided with the reagent, the optical measurement means irradiates the reference cell with light, wherein the reference cell is in a state in which the sample is supplied to the reference cell to obtain first reference data indicating optical characteristics of the reference cell. The optical measurement means irradiates a base portion of the analysis unit with light to obtain second reference data indicating optical characteristics of the base portion. The base portion is a portion at which the reaction cell and the reference cell are not formed and which has a substantially same sectional structure as a portion formed with the reference cell except for the absence of a cell.

Preferably, the data processor executes processing to obtain data on the unreacted sample which indicates optical characteristics of the sample before reaction with the reagent based on the first and the second reference data.

Preferably, the base portions are set at a plurality of positions, and the optical measurement means irradiates the plurality of base portions with light to obtain a plurality of second reference data. The data processor utilizes the plurality of second reference data to obtain the data on the unreacted sample.

Preferably, the optical measurement means performs the operation to irradiate the base portion with light a plurality of times at time intervals to obtain the plurality of second reference data. The data processor utilizes the plurality of second reference data to obtain the data on the unreacted sample.

Preferably, the data processor determines whether or not the color or concentration of the sample is normal based on the data on the unreacted sample.

Preferably, in the case where the sample is blood, the data processor determines that the blood is hemolysis when the absorbance with respect to light of a wavelength around 410 nm in the data on the unreacted sample is lower than that with respect to light of a wavelength around 445 nm.

Preferably, in the case where the sample is blood, the data processor determines that the blood is chyle when the absorbance with respect to light of a predetermined wavelength in the data on the unreacted sample is higher than a predetermined threshold.

Preferably, the data processor corrects the data indicating the optical characteristics of the reaction portion by utilizing the first reference data to obtain correction data indicating more precise optical characteristics of the reaction portion and obtaining measurement of a predetermined item of the sample based on the correction data.

Preferably, in obtaining measurement of a predetermined item of the sample, the data processor performs correction to reduce the inaccuracy of data caused by the dilution of the sample with the reagent and by the changes in color of the sample in accordance with the type of the reagent.

Preferably, the reaction cell, the reference cell and the base portion of the analysis unit are arranged on a same circumference. The optical measurement means is capable of successively irradiating the reaction cell, the reference cell and the base portion with light by rotating the analysis unit relative to the light source for irradiation.

Other features and advantages of the present invention will become more apparent from the description of embodiments of the present invention given below with reference to the accompanying drawings.

BRIEF DESCRIPTION OF THE DRAWINGS

FIGS. 4A and 4B are sectional views of the analysis unit illustrated in FIG. 2.

BEST MODE FOR CARRYING OUT THE INVENTION

Figure 1:
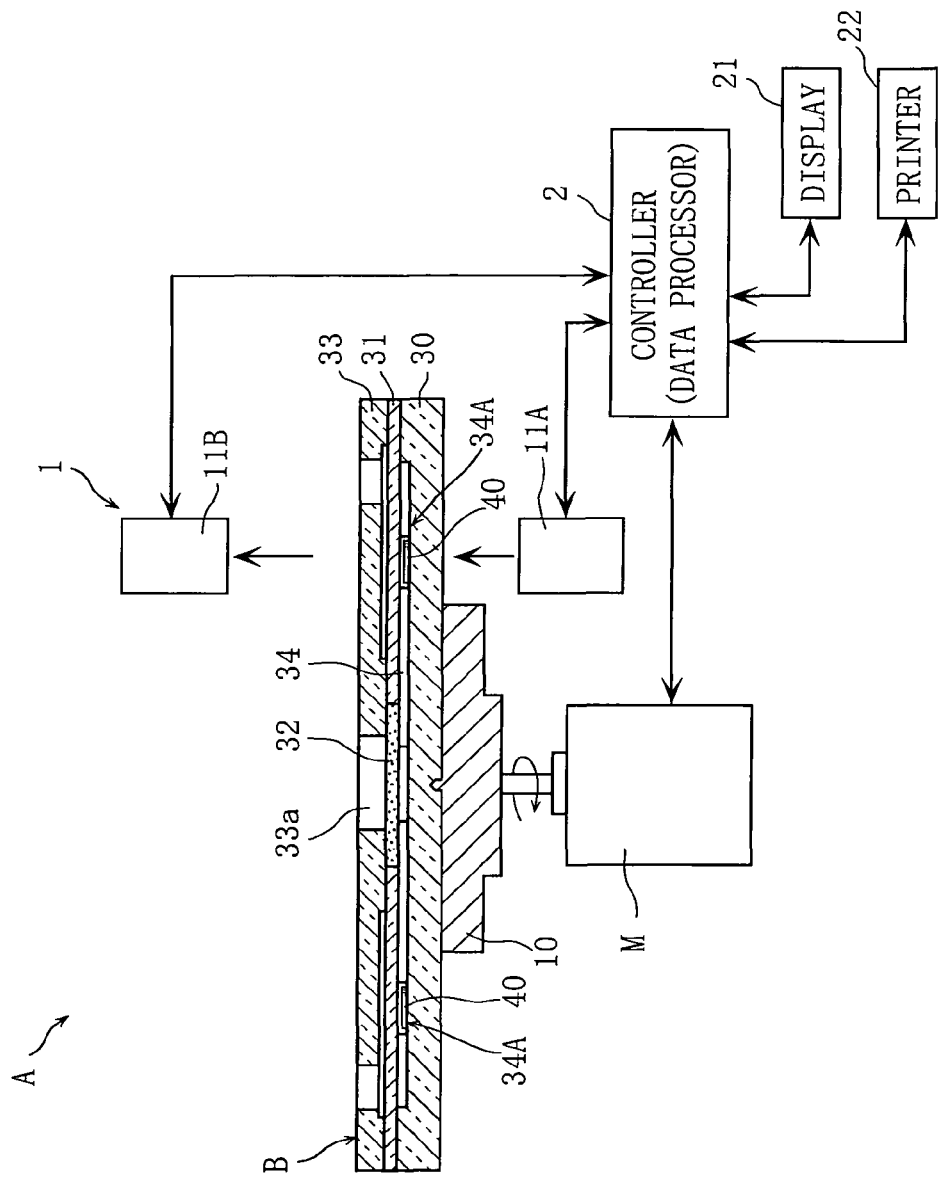
FIG. 1 is an external view illustrating an example of analyzer according to the present invention.

Preferred embodiments of the present invention are described below in detail with reference to the accompanying drawings.

FIGS. 1 to 5 illustrate an analyzer according to the present invention and an example of its related structure. The analyzer A illustrated in FIG. 1 includes an optical measurement unit 1 for measuring the absorbance of a predetermined portion of an analysis unit B, and a controller 2. The controller 2 is structured by using a micro computer and an exemplary data processor as defined by the present invention.

The optical measurement unit 1 includes a support base 10 for supporting an analysis unit B, a light emitting portion 11A and a light receiving portion 11B. The support base 10 is horizontally rotatable by the driving of a motor M to cause the analysis unit B to rotate together. The analysis unit B can be freely mounted on and removed from the support base 10. The light emitting portion 11A includes a plurality of LED light sources (not shown) for emitting light of different peak wavelengths and irradiates a predetermined position of the analysis unit B, which will be described in more detail later, with light from below. The light receiving portion 11B has a light detection function. The light receiving portion 11B receives the light emitted from the light emitting portion 11A and passed upward through the predetermined position of the analysis unit B and outputs a signal of a level corresponding to the intensity of the light received. The signal is transmitted to the controller 2.

The controller 2 performs processing of the data represented by the signals transmitted from the light receiving portion 11B as well as the operation control of each part of the analyzer A. The details will be described later. A display 21 and a printer 22 are connected to the controller 2. The display 21 is structured by using e.g. a liquid crystal panel and is capable of displaying analysis results or various data related thereto on the surface thereof. The printer 22 is used to print such data.

Figure 2:
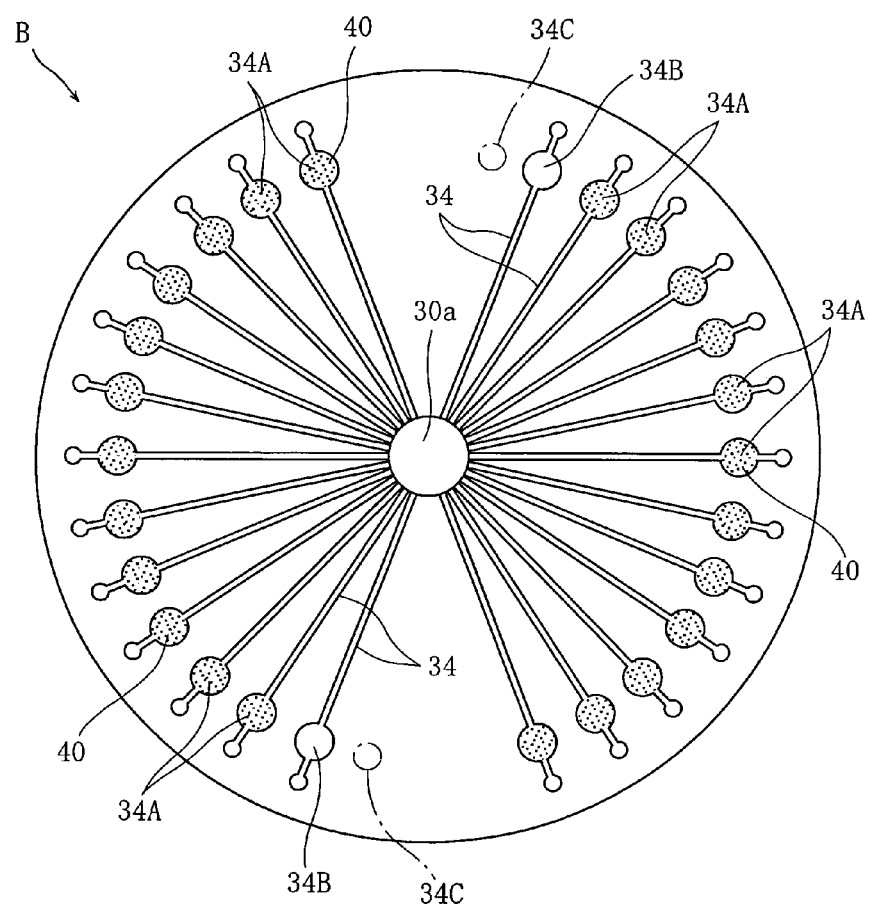
FIG. 2 is a plan view schematically illustrating an example of a main structure of an analysis unit for use in the analyzer illustrated in FIG. 1.

The analysis unit B is generally in the form of a disc and includes a plurality of flow paths 34 extending radially from a center hole 30a, a plurality of reaction cells 34A in which a reagent 40 is provided, a plurality of reference cells 34B in which the reagent 40 is not provided, and a plurality of base portions 34C, as illustrated in FIG. 2. The plurality of reaction cells 34A, the plurality of reference cells 34B and the plurality of base portions 34C are arranged an equal radial distance from the center hole 30a.

Figure 3:
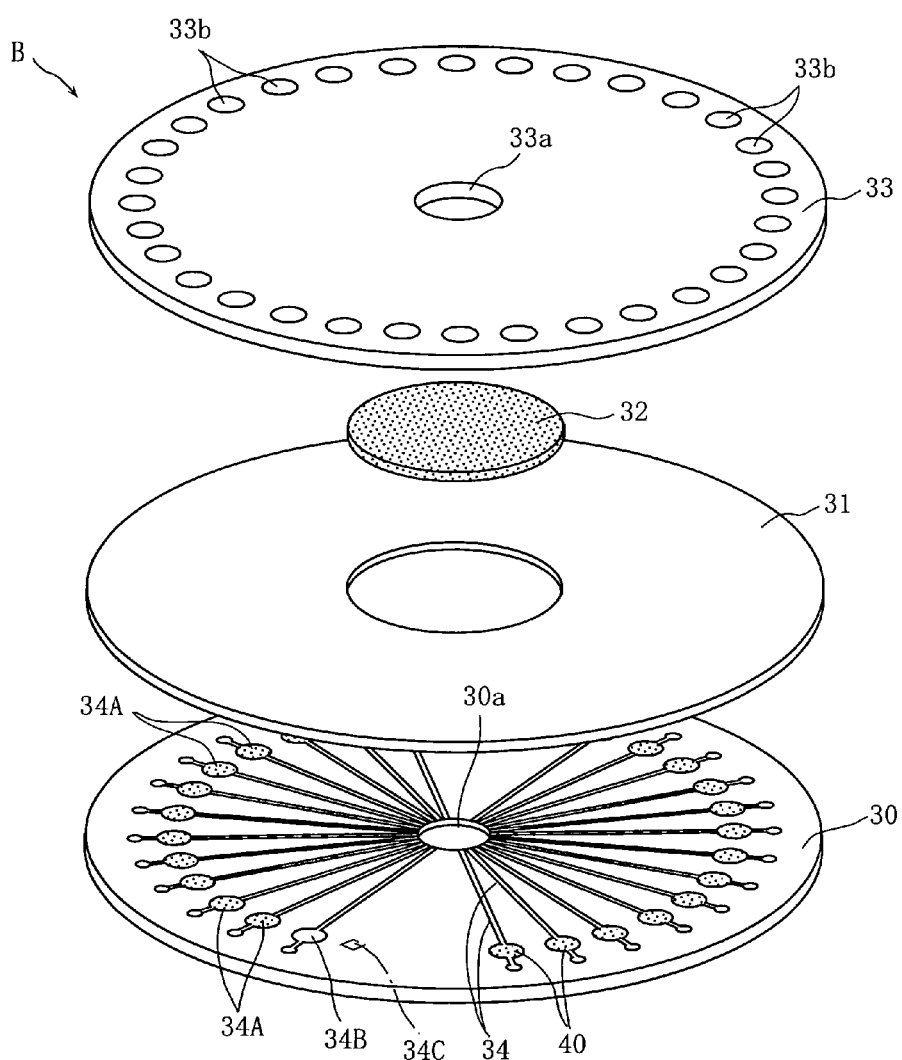
FIG. 3 is an exploded perspective view of the analysis unit illustrated in FIG. 2.

As illustrated in FIGS. 3, 4A and 4B, the analysis unit B is made up of a base plate 30 generally in the form of a disc, a flow path cover 31 and a separation film 32 laminated on the upper surface of the base plate, and a protective cover 33 laminated on flow path cover 31 and separation film 32. As illustrated in FIG. 4A, when blood BL as a sample is applied to a center hole 33a of the protective cover 33, the blood BL passes through the separation film 32 to reach the hole 30a of the base plate 30 and is retained in the hole 30a. The separation film 32 functions to separate the solid components (blood cell components) of the blood BL. The plurality of flow paths 34, each of which is connected to the hole 30a at one end thereof, are defined between the upper surface of the base plate 30 and the flow path cover 31. Before the analysis of the blood BL is started, the other end of each flow path 34 is kept closed, so that the blood BL retained in the hole 33a is prevented from moving toward the other end of each flow path 34. When a hole 31a is made in the flow path cover 31 as illustrated in FIG. 4B so that the other end side of each flow path 34 is exposed to the atmosphere, the blood BL which has retained in the hole 30a moves toward the other end side of the flow path 34 by capillary action as indicated by arrows N1. The blood BL is supplied into the reaction cell 34A, which is provided at an intermediate portion of each flow path 34, and reacts with the reagent 40. The operation of making a hole 31a in the flow path cover 31 may be performed by providing a laser light source (not shown) in the optical measurement unit 1 and applying a laser beam to the flow path cover 31 through the hole 33b of the protective cover 33, for example.

Figure 5:
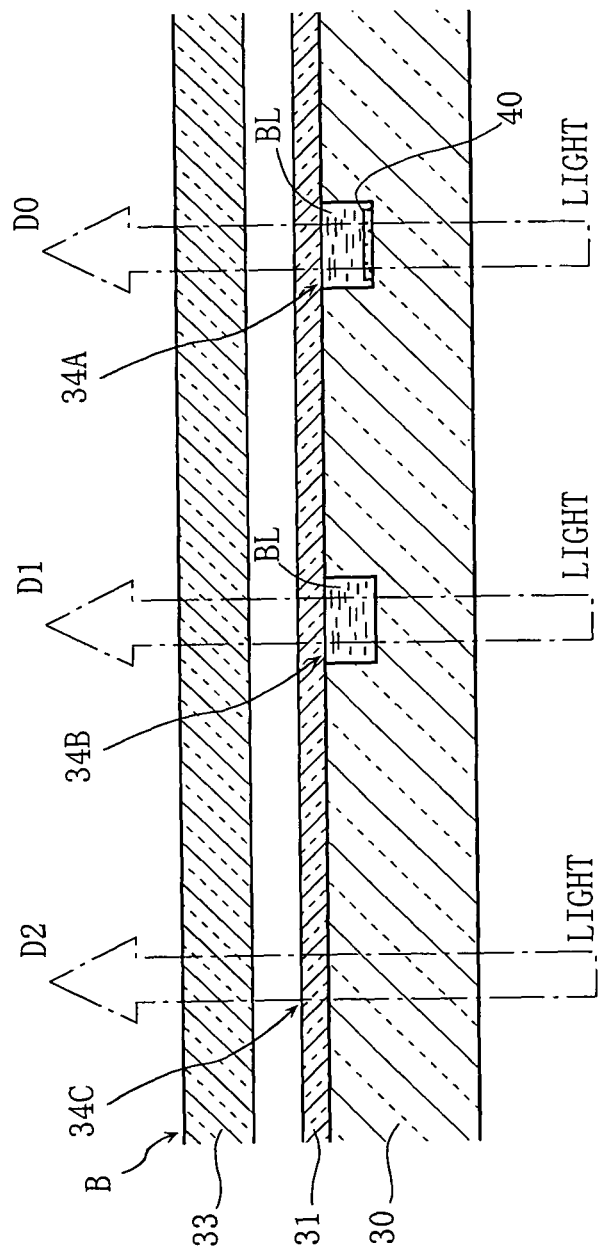
FIG. 5 is a sectional view illustrating a principal portion of an example of a reaction cell, a reference cell and a base portion of the analysis unit.

The reaction cells 34A are formed by making a portion of each flow path 34 wider than other portions. The reagent 40 is in the form of a solid which dissolves when blood BL is supplied thereto and contains a component which develops a color upon reaction with a particular component contained in the blood BL. In this embodiment, to perform measurement with respect to a plurality of components of the blood BL, a plurality of kinds of reagents 40 which differ from each other in components or composition are used. As illustrated in FIG. 5, in the analyzer A, when a reaction portion of the blood BL and the reagent 40 is formed in the reaction cell 34A, the reaction portion is irradiated with light to obtain data D0 indicating the light absorption characteristics of the reaction portion. However, the data D0 do not solely indicate the light absorption characteristics of the reaction portion but are influenced by the light absorption characteristics of the base plate 30, the flow path cover 31 and the protective cover 33.

The reference cells 34B differ from the reaction cells 34A in that the reagent 40 is not provided in the reference cells, as noted before, but are similar to the reaction cells 34A in other points. Specifically, the depth and width of the reference cells 34B are approximately equal to those of the reaction cells 34A, and the blood BL is supplied also into the reference cells 34B. With the blood BL supplied to the reference cells 34B, the analyzer A irradiates this portion with light to obtain the first reference data D1 indicating the light absorption characteristics of this portion.

The base portions 34C are the portions at which the reaction cells and the reference cells 34A, 34B are not formed and which are determined to be a target portion of absorbance measurement. The analyzer A irradiates the base portion 34C with light to obtain the second reference data D2 indicating the light absorption characteristics of this portion. Except for the presence or absence of the cells, the base portion 34C and the portions formed with the reaction cells or the reference cells 34A, 34B have the substantially same sectional structure. Specifically, the reaction cells and the reference cells 34A, 34B are provided by forming a groove in the upper surface of the base plate 30 and covering the top of the groove with the flow path cover 31. On the other hand, the base portion 34C is a portion at which the upper surface of the base plate 30 is covered with the flow path cover 31 without forming a groove. The thickness and material of the base plate 30 and the flow path cover 31 at the base portion 34C are made as equal as possible to those at the portions formed with the cells 34A, 34B. Since the measurement light passes through the protective cover 33 provided on the flow path cover 31, the thickness and material of the protective cover are also made uniform. For instance, the base plate 30 and the protective cover 33 are made of transparent polystyrene, whereas the flow path cover 31 is made of a transparent PET film.

In other words, as illustrated in FIG. 5, the reaction portion 34A of analysis tool B has a structure including, in this order: substrate 30, reagent 40, blood BL, flow path cover 31, and protective cover 33. Furthermore, as also illustrated in FIG. 5, the reference portion 34B of analysis tool B has a structure including, in this order: substrate 30, blood BL, flow path cover 31, and protective cover 33; that is, the reference portion 34B has substantially the same structure as the reaction portion 34A, without the reagent 40. Additionally, as further illustrated in FIG. 5, the base portion 34C of analysis tool B has a structure including, in this order: substrate 30, flow path cover 31, and protective cover 33; that is, the base portion 34C has substantially the same structure as the reference portion 34B, without the cell containing blood BL.

Figure 7:
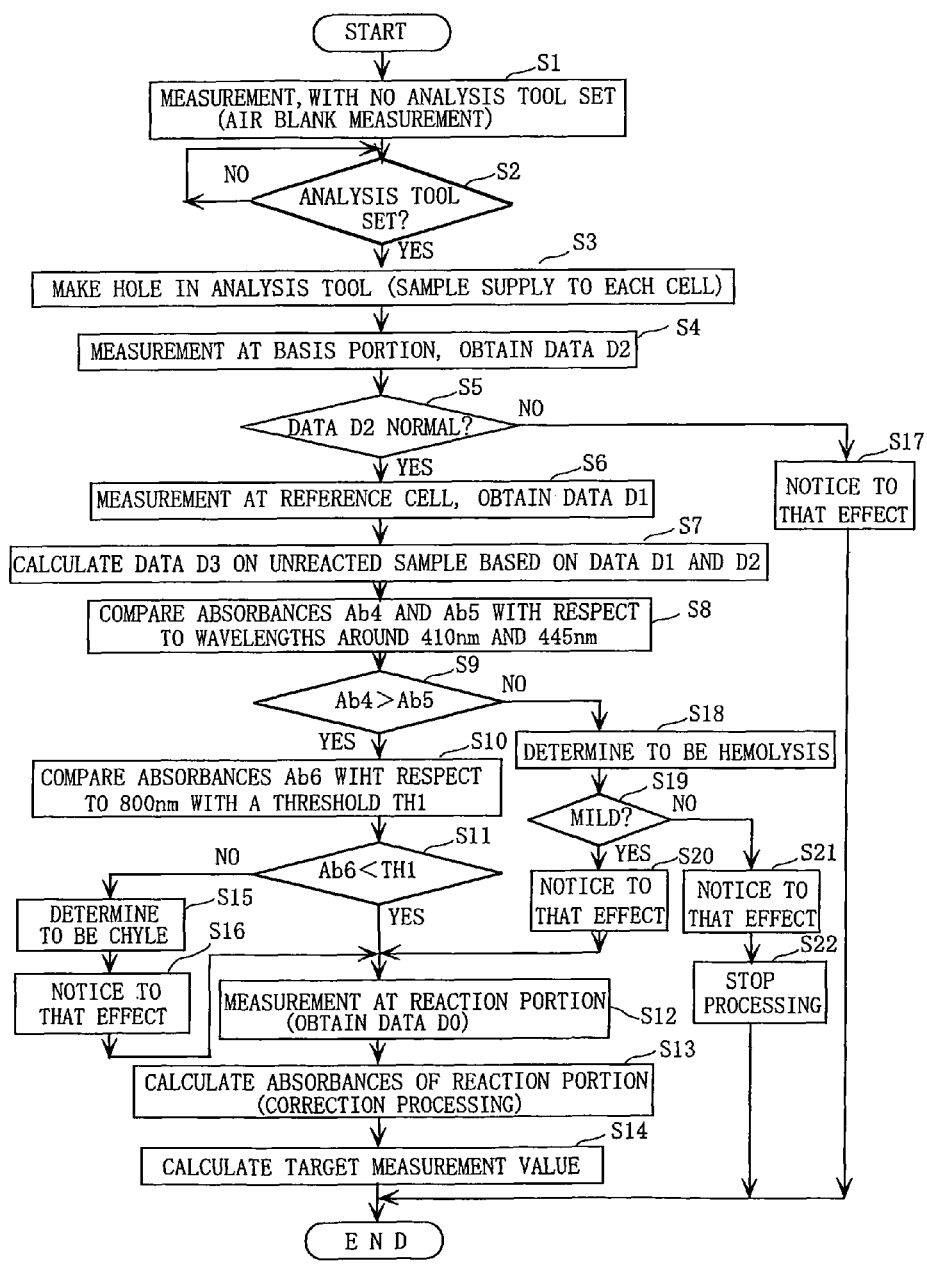
FIG. 7 is a flowchart illustrating an example of data processing process by a controller of the analyzer illustrated in FIG. 1.

An example of method for analyzing the blood BL using the analysis unit B and the analyzer A is described below. An example of data processing process by the controller 2 of the analyzer A is also described with reference to the flowchart of FIG. 7.

First, in the state in which the analysis unit B is not set on the support base 10, the controller 2 drives the light emitting portion 11A to perform optical measurement (S1). In this optical measurement, data are obtained which indicates the light absorption characteristics of an air space between the light emitting portion 11A and the light receiving portion 11B. These data are to be utilized for determining whether or not the values of the second reference data D2 obtained in a later step are proper. Then, when the analysis unit B is set on the support base 10, the controller 2 drives the above-described laser light source to execute the operation to make a hole 31a in the flow path cover 31 of the analysis unit B, as described in FIG. 4B (S2:YES, S3). By this operation, the blood BL, which has been applied to the hole 33a of the analysis unit B, moves in the flow path 34. The above-described operation to make a hole is successively performed with respect to each of the plurality of flow paths 34 while successively rotating the support base 10 and the analysis unit B through a predetermined angle. By this operation, the blood BL is successively supplied to each of the reaction cells 34A and reference cells 34B.

Then, the controller 2 executes the operation to irradiate the base portion 34C of the analysis unit B with light to obtain the second reference data D2 indicating the light absorption characteristics of this portion (S4). Then, whether or not the values of the second reference data D2 are normal is determined (S5). This determination is made based on whether or not the value of the second reference data D2 is within a predetermined range relative to the value of the data on the light absorption characteristics of the airspace obtained in the step S1. When the values of the second reference data are not within the predetermined range, it is determined that the values are not normal because of any error. When it is determined that the values are not normal, a notice to that effect is given, and the analysis processing is stopped (S5:NO, S17). For instance, the notice is given by displaying a predetermined message on the display 21. This holds true for other notices which will be described later.

When the values of the second reference data D2 are normal, the controller 2 executes the operation to irradiate the reference cell 34B with light to obtain the first reference data D1 (S5:YES, S6). Then, based on the first and the second reference data D1 and D2, the controller 2 calculates the data D3 on the unreacted sample (S7). The data D3 on the unreacted sample are e.g. the data indicating the absorbance of the blood BL itself (i.e., the blood BL before the reaction with the reagent 40) and are calculated as follows. First, the respective absorbances Ab1 and Ab2 of the reference cell 34B and the base portion 34C are calculated based on the first reference data D1 and the second reference data D2. Then, the absorbance Ab3 of the blood BL is found by the formula: Ab3=Ab1−Ab2, for example.

Figure 6:
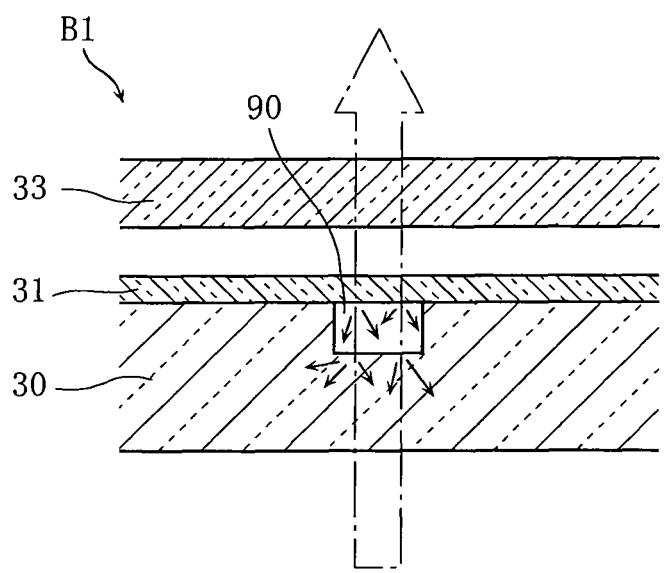
FIG. 6 is a sectional view illustrating a principal portion of a comparative example relative to the present invention.

Unlike the present embodiment, as a method to obtain the data D3 on the unreacted sample, it may be considered to use the reference data D9 shown in FIG. 6 as a comparative example. However, the present embodiment is more favorable than the comparative example, because the comparative example has the following drawbacks.

In the comparative example shown in FIG. 6, a cell 90 to which the blood BL is not to be supplied is formed in the analysis unit B 1, and the reference data D9 are obtained by irradiating this portion with light. In this comparative example, the light traveling to the cell 90 is scattered and reflected at the interface between the air space in the cell 90 and the base plate 30. The light is scattered and reflected also at the interface between the air space and the flow path cover 31. Since a large amount of light is scattered and reflected in this way, the reference data D9 do not precisely reflect the absorbance of the portion formed with the cell 90. Thus, when the data D3 on the unreacted sample are computed based on the reference data D9 and the first reference data D1 unlike the present embodiment, incorrect data are obtained.

By contrast, since the base portion 34C of the present embodiment is not formed with a cell as illustrated in FIG. 5, such scattering and reflection of light as seen in the comparative example does not occur or hardly occurs. Thus, the second reference data D2 precisely reflect the absorbance of the base portion 34C itself. Because of the absence of a cell, the thickness of the base plate 30 is larger at the base portion 34C than at the portion formed with the reference cell 34B. Thus, when the second reference data D2 are compared with the first reference data D1, the respective absorbances differ from each other, which is not only because of the presence or absence of blood but also because of the above-described difference in thickness of the base plate 30. However, the depth of the reference cell 34B is e.g. about 100 μm, and the absorbance of the base plate 30 corresponding to a thickness of about 100 μm is small and negligible. When the base plate 30 has a high light transmittance, the absorbance is smaller still.

Thus, the second reference data D2 precisely indicate the optical characteristics of the base portion 34C and are suitable as the correct data indicating the optical characteristics of the background of the reference cell 34B. Thus, based on the first and the second reference data D1 and D2, the data D3 on the unreacted sample which corresponds to the actual absorbance of the blood BL is properly obtained. As to the reference cell 34B, light is less scattered and reflected at this cell than in the comparative example of FIG. 6, because the blood BL is supplied to the cell. Thus, the first reference data D1 also precisely reflect the actual absorbance of the portion formed with the reference cell 34B, and hence, are suitable for the obtainment of precise data D3 on the unreacted sample.

To obtain the data D3 on the unreacted sample, it is possible to utilize a plurality of second reference data D2 obtained by irradiating each of the plurality of base portions 34C with light. In the case where only a single base portion 34C is provided in the analysis unit B unlike the present embodiment, the second reference data D2 may not be obtained properly when dust or the like is on the base portion 34C, for example. In contrast, when a plurality of second reference data D2 are obtained by irradiating each of the plurality of base portions 34C with light, such a problem is eliminated and the data D3 on the unreacted sample are obtained more precisely. As a method to utilize the plurality of second reference data D2, an approximation curve using time as a parameter may be obtained based on a plurality of absorbance values obtained from the plurality of second reference data D2, and the values of the approximation curve may be used. Since the arrangement of this embodiment also includes a plurality of reference cells 34B, a plurality of first reference data D1 can also be obtained, which makes the data D3 on the unreacted sample more precise. Though not illustrated in FIG. 7, a plurality of first and second reference data D1 and D2 can be obtained by repeatedly irradiating the base portion 34C or the reference cell 34B with light at appropriate time intervals. With this method, the plurality of first and second reference data D1 and D2 correspond to changes with time in each part of the analysis unit B (changes in temperature, for example), which makes the data D3 on the unreacted sample more precise.

After the data D3 on the unreacted sample are obtained, the controller 2 determines based on the data D3 whether or not the blood BL is a hemolysis sample. Specifically, in the data D3 on the unreacted sample, the controller 2 compares the absorbance Ab4 with respect to light having a wavelength around 410 nm and the absorbance Ab5 with respect to light having a wavelength around 445 nm. When the relation Ab4<Ab5 does not hold, the controller 2 determines that the blood BL is a hemolysis sample (S8,S9:NO, S18). While the peak wavelength of the absorption spectrum of hemoglobin in blood BL is 410 nm, the peak wavelength of the absorption spectrum of bilirubin is 445 nm. Thus, the absorbances Ab4 and Ab5 with respect to these wavelengths should be Ab4<Ab5. Thus, when this relation does not hold, the blood BL is determined to be a hemolysis sample. To easily obtain the absorbances Ab4 and Ab5, two different LED light sources which respectively emit light having a peak wavelength around 410 nm and a peak wavelength around 445 nm, respectively, are provided in the light emitting portion 11A. By individually turning on the two LED light sources, the respective absorbances are obtained individually.

When the blood BL is determined to be a hemolysis sample, the controller 2 determines whether or not the hemolysis is of a mild degree lower than a predetermined reference. When the hemolysis is mild, the controller gives a notice to that effect and then proceeds to the subsequent analysis step (S19:YES, S20). On the other hand, when the hemolysis is determined to be severe, a notice to that effect is given, and the analysis processing is stopped (S19:NO, S21, S22).

The controller 2 further determines whether or not the blood BL is a chyle sample. For instance, in the data D3 on the unreacted sample, the controller 2 compares the absorbance Ab6 with respect to light in a wavelength band of e.g. 800 nm with a predetermined threshold TH1. When the relation Ab6<TH1 does not hold, the controller determines that the sample is a chyle sample (S10,S11:NO, S15). Since chyle blood is turbid or milky white, it has a high absorbance with respect to light in a very wide band of wavelengths, particularly in a long-wavelength band. Thus, when the sample is not chyle, the relation Ab6<TH1 holds, and when this relation does not hold, the sample is determined to be chyle. When the sample is determined to be chyle, the controller 2 gives a notice to that effect and then proceeds to the subsequent analysis step (S15, S16). Alternatively, in this case, similarly to the case of hemolysis, the degree of chyle may be examined and a different step may be performed depending on whether or not the degree is mild.

As described above, in this analysis method, the presence or absence of hemolysis and chyle in the blood BL is determined based on the data D3 on the unreacted sample. Herein, the data D3 on the unreacted sample are the data indicating the absorbance of the blood BL itself obtained based on the first and the second reference data D1 and D2. This ensures correct determination of the presence or absence of hemolysis and chyle. Thus, it is possible to prevent the analysis result of the blood BL from being shown as a correct result without any notice, and to prevent an analysis wherein the hemolysis or chyle have been overlooked.

After the above-described step, the controller 2 executes the operation to irradiate the reaction cell 34A with light to obtain the data D0 on the reaction portion (S12). Then, the controller 2 corrects the data D0 on the reaction portion by utilizing the first reference data D1, calculates the absorbance of the reaction portion of the blood BL and the reagent 40, and then obtains a target measurement value such as the concentration of a particular component in the blood BL (S13, S14). The first reference data D1 correspond to, or serve as an alternative to, the blank correction data in the conventional technique. Since the first reference data are obtained by irradiating the reference cell 34B which is not provided with the reagent 40 with light as noted before, the values are not influenced by the light transmittance of the reagent 40 and are hence precise. Specifically, even when the reagent 40 has a surface which readily scatters and reflects light, such scattering and reflection of light by the reagent 40 does not occur in irradiating the reference cell 34B with light. Thus, a large amount of light passes through the reference cell 34B, so that the value of the first reference data D1 obtained is precise.

In the above-described processing, the dilution of the blood BL with the reagent 40 is not taken into consideration. Though not illustrated in FIG. 7, in the step S14 for obtaining a measurement value, the controller 2 performs correction to correct the inaccuracy of data caused by the dilution of the blood BL with the reagent 40 and by the changes in color of the blood BL in accordance with the kind of the reagent. The data for this correction processing can be prepared in advance by conducting an examination and then stored in the controller 2. This correction processing further enhances the measurement accuracy.

The present invention is not limited to the foregoing embodiment. The specific arrangement of each step of the sample analysis method according to the present invention can be modified in various ways. Further, the specific structure of each part of the analyzer according to the present invention can be modified in various ways.

The sample in the present invention is not limited to blood, and urine and various other substances can be used as the sample. The reagent is selected appropriately in accordance with the kind of the sample or the items to be measured. The specific structure of the analysis unit used for the analysis is not particularly limited. For instance, a reaction cell, a reference cell and a base portion can be arranged on a straight line. In this case, these portions can be successively irradiated with light by moving the analysis unit and the optical measurement unit linearly relative to each other.

The invention claimed is:

1. A method of analyzing a sample comprising:
   providing an analysis unit including a base plate comprising a transparent substrate and a transparent cover, the base plate including:
      a reaction portion having at least one reaction cell including a reagent and a sample between the transparent substrate and the transparent cover,
      at least one reference portion having a reference cell including the sample between the transparent substrate and the transparent cover, and
      at least one base portion which does not comprise a cell,
   wherein the reference portion, the reaction portion, and the base portion are located in the base plate and the base portion is located at a position of the base plate where the reaction cell and the reference cell are not located,
   irradiating the reaction cell with light from a light source to obtain a reaction data from an optical detector, the reaction data indicating optical characteristics of the reaction portion;
   irradiating the reference cell with light from the light source to obtain a first reference data from the optical detector, the first reference data indicating optical characteristics of the reference portion;
   irradiating the base portion with light from the light source to obtain a second reference data from the optical detector, the second reference data indicating optical characteristics of the base portion;
   detecting the emitted light from the reaction cell, the reference cell, and the base portion, the detected light respectively being light that has passed through the reaction cell, the reference cell, or the base portion; and
   correcting the first reference data using the second reference data to obtain a sample data, the sample data indicating optical characteristics of the sample,
   wherein the base plate and the light source are movable relative to one another, and
   wherein a respective depth of the reaction cell and the reference cell is about 100 μm.

2. The method according to claim 1, wherein the step of correcting comprises:
   comparing, by a data processor, the first reference data and the second reference data to obtain the sample data and determine whether the color or concentration of the sample is within a predetermined range,
   wherein the step of comparing comprises:
      calculating a first absorbance Ab1 and a second absorbance Ab2 respectively based on the first reference data and the second reference data, and
      calculating a sample absorbance Ab3, which is a kind of the sample data, based on the following formula: Ab3=Ab1−Ab2.

3. The method according to claim 2, further comprising:
   correcting, by the data processor, the reaction data by utilizing the sample data.

4. An analyzer comprising:
   an optical measurement unit including a light source configured to emit light and an optical detector configured to receive the emitted light;
   an analysis unit including a base plate comprising a transparent substrate and a transparent cover, the base plate including:
      a reaction portion having at least one reaction cell including a reagent and a sample between the transparent substrate and the transparent cover,
      at least one reference portion having a reference cell including the sample between the transparent substrate and the transparent cover, and
      at least one base portion which does not comprise a cell,
      wherein the reference portion, the reaction portion, and the base portion are located in the base plate and the base portion is located at a position of the base plate where the reaction cell and the reference cell are not located; and
   a data processor operatively connected to the optical measurement unit and configured to process data,
   wherein the optical measurement unit is configured to irradiate the reaction portion with light to obtain a reaction data, the reaction data indicating optical characteristics of the reaction portion, to irradiate the reference portion with light to obtain a first reference data, the first reference data indicating optical characteristics of the reference portion, and to irradiate the base portion with light to obtain a second reference data, the second reference data indicating optical characteristics of the base portion, wherein the detected light is light that has passed through the reaction cell, the reference cell, or the base portion, wherein the base plate and the light source are movable relative to one another, and wherein a respective depth of the reaction cell and the reference cell is about 100 μm.

5. The analyzer according to claim 4, wherein the data processor is configured to obtain a sample data by comparing the first reference data and the second reference data, the sample data indicating optical characteristics of the sample.

6. The analyzer according to claim 5, wherein:
the at least one base portion includes a plurality of base portions located at a plurality of positions arranged at a same radial distance from a center of the base plate;
the optical measurement unit is configured to rotate the analysis unit;
the optical measurement unit is further configured to move the plurality of base portions sequentially to a position at which the light source and the optical detector are located;
the optical measurement unit is further configured to irradiate the plurality of base portions with the light to obtain a plurality of respective second reference data; and
the data processor is configured to obtain the sample data based on the plurality of respective second reference data.

7. The analyzer according to claim 5, wherein:
the optical measurement unit is configured to irradiate the base portion with light a plurality of times at time intervals to obtain a plurality of second reference data; and
the data processor is configured to obtain the sample data based on the plurality of second reference data.

8. The analyzer according to claim 5, wherein:
the data processor is configured to determine whether the color or concentration of the sample is within a predetermined range by comparing the sample data with a specific predetermined wavelength range.

9. The analyzer according to claim 5, wherein:
the data processor is configured to calculate a second absorbance Ab2 based on the second reference data, a sample absorbance Ab3 based on the sample data, and an absorbance of the reaction cell Ab7 based on the reaction data; and to correct the absorbance of the reaction cell Ab7 based on the following formula to obtain a reaction absorbance Ab8: $Ab8=Ab7-Ab3-Ab2$, wherein each of the absorbances Ab2, Ab3, and Ab7 are absorbances at a same wavelength.

10. The analyzer according to claim 4, wherein:
the sample is blood;
the light source comprises a first light emitter configured to emit a first light having a wavelength of approximately 410 nm, and a second light emitter configured to emit a second light having a wavelength of approximately 445 nm;
the data processor is configured to determine that the blood is hemolysis when an absorbance by the sample of the first light is lower than an absorbance by the sample of the second light;
when the blood is determined to be hemolysis, the data processor gives a notice or stops measuring; and
when the blood is determined not to be hemolysis, the data processor continues measuring.

11. The analyzer according to claim 4, wherein:
the sample is blood;
the light source is configured to emit a first light having a predetermined wavelength;
the data processor is configured to determine that the blood is chyle when an absorbance by the sample of the first light is higher than a predetermined threshold;
the predetermined wavelength is selected from wavelengths at which the blood does not have significant absorption;
when the blood is determined to be chyle, the data processor gives a notice or stops measuring; and
when the blood is determined not to be chyle, the data processor continues measuring.

12. The analyzer according to claim 4, wherein:
the optical measurement unit is configured to rotate the analysis unit; and
the analysis unit is positioned such that a portion of the analysis unit is located between the light source and the optical detector.

* * * * *